Figure 6:
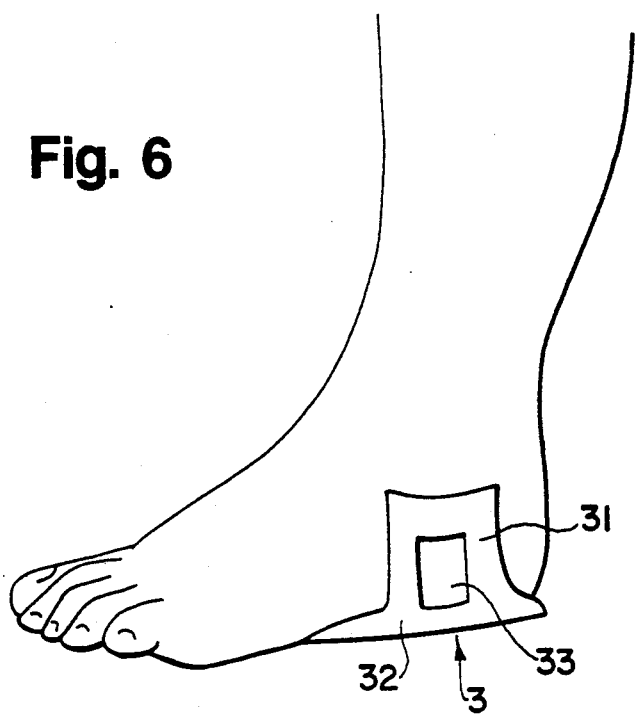

United States Patent [19]

Amrein

[11] Patent Number: 5,099,860
[45] Date of Patent: Mar. 31, 1992

[54] ORTHOTIC DEVICE FOR THE DYNAMIC TREATMENT OF TEARING OR STRAINING OF THE LIGAMENTS OF THE LATERAL ANKLE

[76] Inventor: Max Amrein, 2, Chemin de la Roche, CH-1020 Renens, Switzerland

[21] Appl. No.: 557,453

[22] Filed: Jul. 25, 1990

[30] Foreign Application Priority Data

Aug. 3, 1989 [CH] Switzerland .......................... 2876/89

[51] Int. Cl.$^5$ ............................................... A61F 5/37
[52] U.S. Cl. ...................... 128/882; 602/27; 602/65
[58] Field of Search .................... 128/80, 80 D, 80 H, 128/87 R, 882, 869, 166

[56] References Cited

U.S. PATENT DOCUMENTS

| | | | |
|---|---|---|---|
| 3,133,544 | 5/1964 | Coplans | 128/80 D |
| 4,523,394 | 6/1985 | Lindh et al. | 128/166 X |
| 4,686,994 | 8/1987 | Harr et al. | 128/80 D X |
| 4,719,926 | 1/1988 | Nelson | 128/80 H |
| 4,729,370 | 3/1988 | Kallassy | 128/80 H X |

FOREIGN PATENT DOCUMENTS 8809649 12/1988 France .......................... 128/166

Primary Examiner—Robert A. Hafer
Assistant Examiner—Brian E. Hanlon
Attorney, Agent, or Firm—Tilton, Fallon, Lungmus

[57] ABSTRACT

An improved orthotic device for treating torn or sprained ankle ligaments has a leggings-type bandage formed of medial, lateral, and plantar textile cloth sections closable upon one another by closing bands, medial and lateral splints insertable within splint-mounting bands which are carried by the medial and lateral textile cloth sections, and a separate eversion wedge which can be adjustably applied to the bandage. The eversion wedge has two walls formed approximately perpendicular to one another, with the plantar wall decreasing in a wedge-shaped manner away from the lateral wall thereof. An anti-plantar flexion band formed from a curved strip can be fastened so as to extend away from the lateral side and under the plantar portion of the bandage and terminates at its two ends in adhesion strips, both of which can be adhered to the medial splint-mounting band.

4 Claims, 3 Drawing Sheets

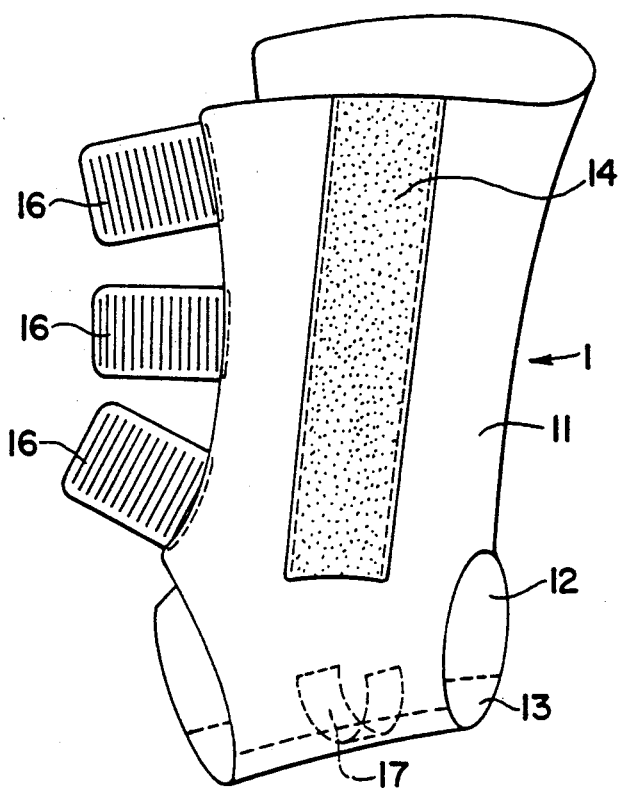
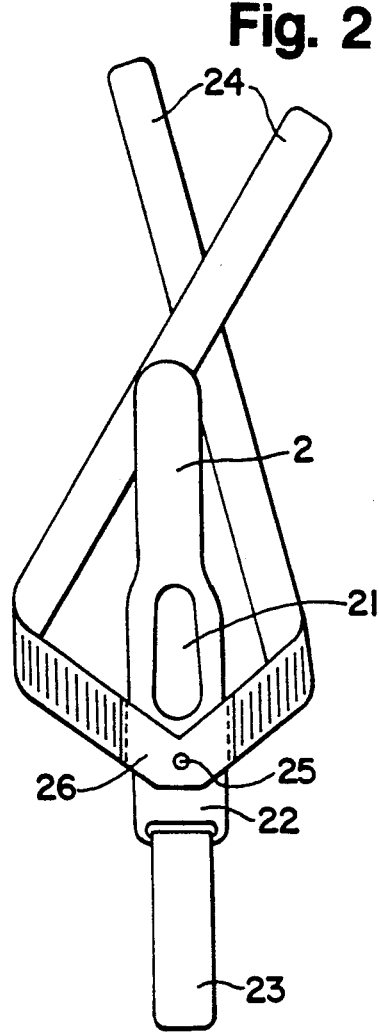
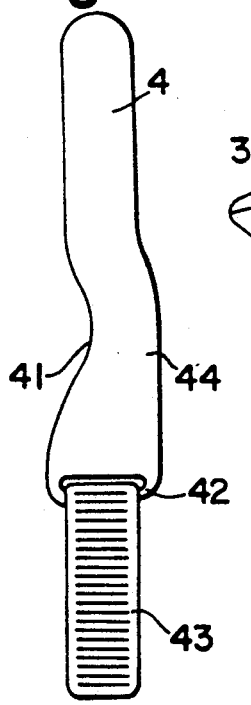
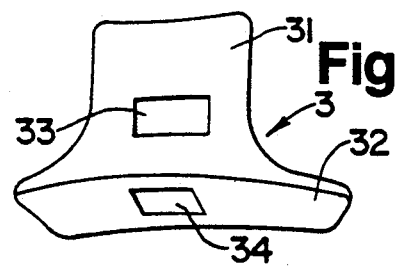
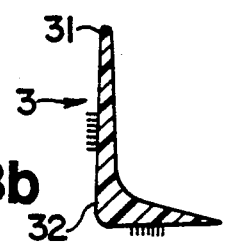
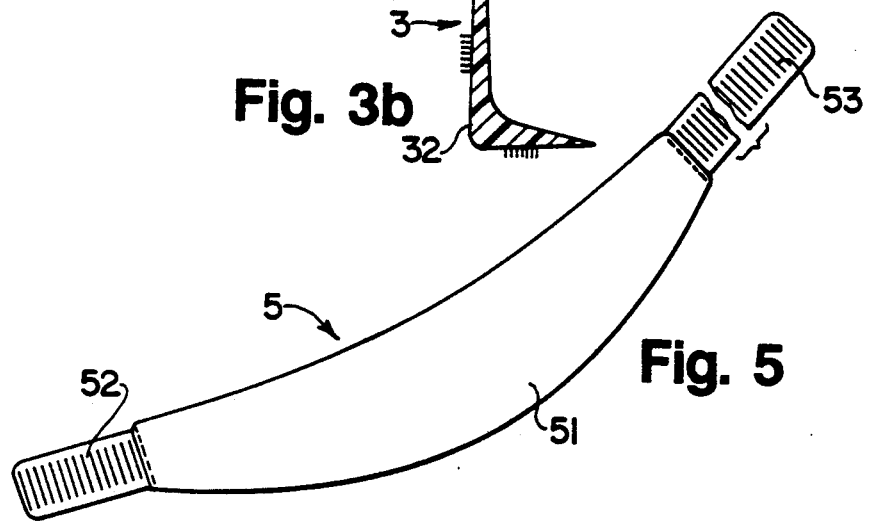

ORTHOTIC DEVICE FOR THE DYNAMIC TREATMENT OF TEARING OR STRAINING OF THE LIGAMENTS OF THE LATERAL ANKLE

Orthotic devices for the treatment of ligament injuries at the lateral ankles have long been known in orthopedic technology. In this technology, however, the primary concern was with fixation, which corresponds to a static treatment. This was generally carried out through the application of a cast or by means of relatively rigid orthotic devices, in which splinting had particular prominence. As is known, however, static treatment leads to an extension of the treatment time, and necessitates a relatively long and intensive aftercare with massages and motion therapies. An orthotic device for the dynamic treatment of ligament injuries which could satisfy all needs was not known, however.

It is therefore an object of the present invention to create an orthotic device, which is particularly suited for the dynamic treatment of ligament injuries on the lateral ankle, whereby, in particular, an eversion of the calcaneal portion of the foot is ensured and, if necessary, the plantar flexion of the foot can be prevented. An orthotic device made in accordance with the present invention solves this problem.

One preferred embodiment of the invention is depicted in the attached drawings, and is explained in detailed form in the following description.

Figure 7:
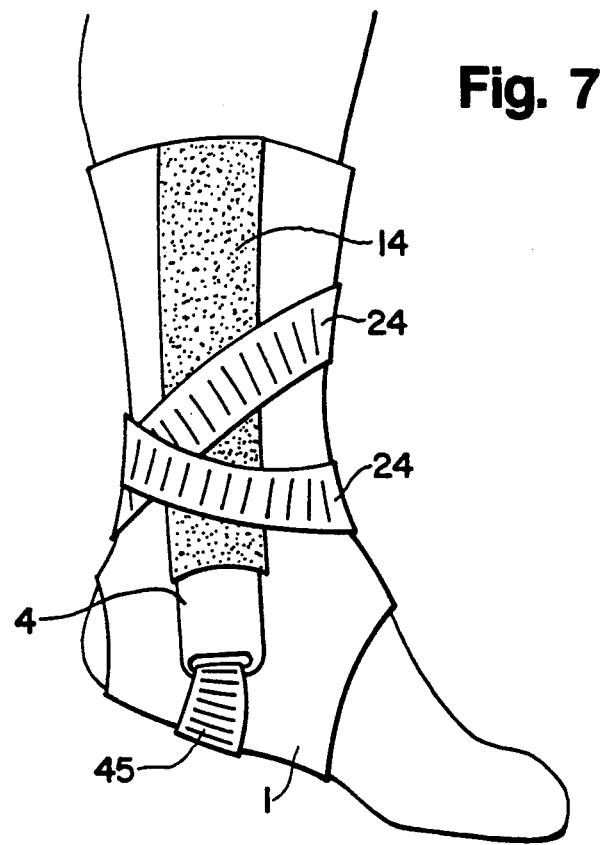
Figure 8:
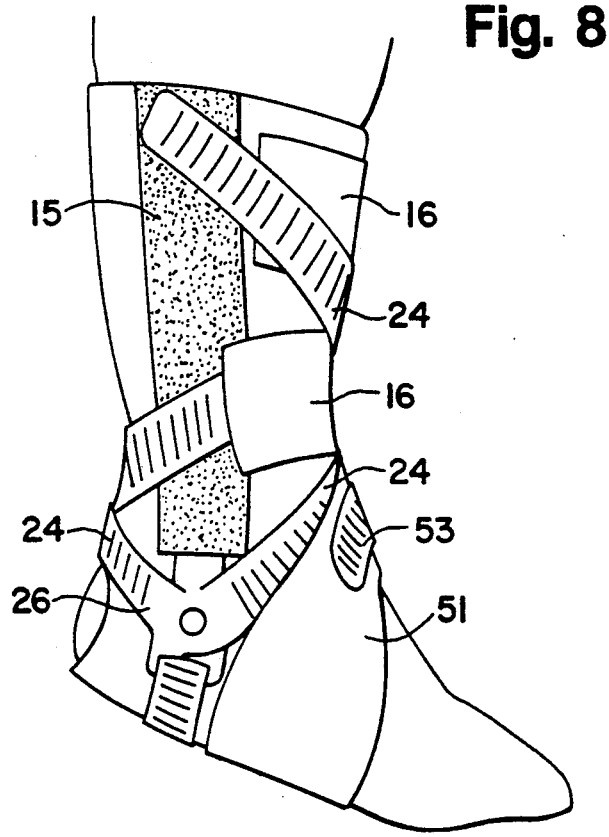
Figure 9:
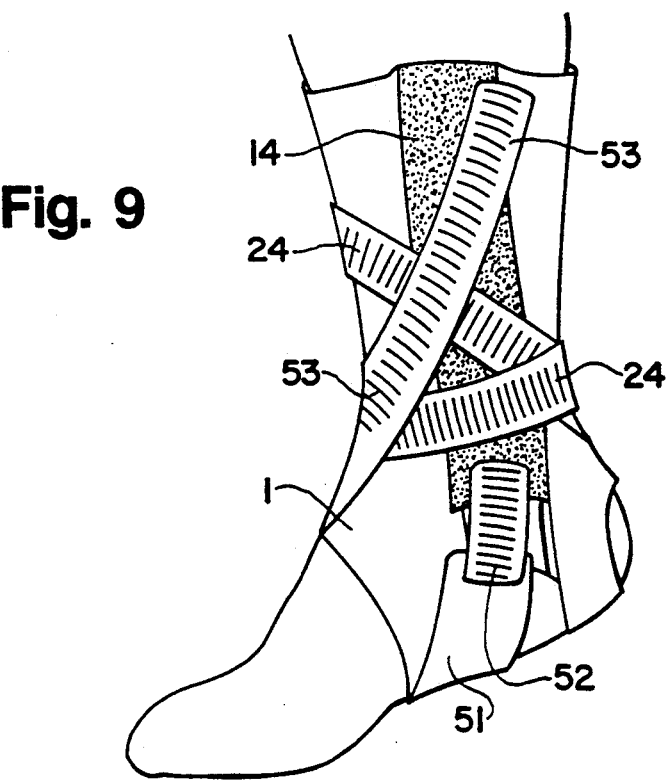

The figures depict the following:

FIGS. 1 to 5: The individual parts of the orthotic device;

FIG. 6: The arrangement of the eversion wedge on a foot which is to be treated;

FIG. 7: The orthotic device, viewed from the medial side, in the position of use, without any anti-plantar flexion band;

FIG. 8: The same arrangement of the lateral side, viewed with an anti-plantar flexion band; and FIG. 9: The arrangement in accordance with FIG. 8, viewed from the medial side.

The individual parts of the orthotic device will first of all be described without reference to function, and their functional significance will then be illustrated.

The terms medial and lateral will be used frequently in the following description. The term 'medial' refers to the inner side of the foot, while the term 'lateral' refers to the outer side of the foot. In reference to the individual elements of the orthotic device, these terms are used, of course, in reference to the foot which is protected with the orthotic device.

Furthermore, the expression 'eversion' will be used repeatedly. In event of a foot sprain, the foot is bent inwardly, whereby the outer ankle ligaments, that is to say, the lateral ligaments, can be damaged. This movement is termed 'inversion'. The damaged foot consequently tends to inversion. The opposite movement is termed 'eversion'.

The tendency of the forefoot to hang downwardly, which appears after a ligament injury, is termed 'plantar flexion'.

The base element of the present orthotic device is the ankle bandage (1) depicted in FIG. 1. This is composed of three cloth pieces which are cut to order and sewn together; specifically, a medial (11) and a lateral (12) cloth piece, and a plantar cloth piece (13) which connects the above two. The legging thus formed, which is closed at the bottom, is made from an elastic, double-layer knitted textile with an interposed padding layer, and is provided with a perforation for the necessary air circulation.

On the outer side of the bandage, both medially and laterally, an adhesion band (14, 15) proceeding in the longitudinal direction of the leg portion of the bandage (1), is sewed on with the adhesion-side which is directed outwardly. Corresponding to its function, this should be designated as the splint-mounting band, with reference figure (14) on the medial side (here in FIG. 1, the side viewed), and (15) on the lateral side (not visible in FIG. 1, but see FIG. 8). The splint-mounting bands (14, 15) are stitched together with the bandage (1), and are seamed with the upper edge of the bandage in a snug manner. Three elastic adhesion bands, which serve as the sealing bands (16) of the bandage, are attached to the medial cloth piece (11) and fit closely in the use position medially on the lower leg. Corresponding counter-bands are sewed on externally to the lateral cloth piece (12). On the outer side of the bandage (1), on the lateral cloth piece (12) and on the plantar cloth piece (13), a counter-band serving for the adhesion, which acts as a positioning band (17), is sewed in, as is indicated by dotted lines. This positioning band (17) extends approximately from the area below the ankle which is to be bandaged, up to approximately the center of the sole area.

A lateral splint (2) depicted in FIG. 2, which is slightly widened in the ankle area and has a recess (21) formed there which is adapted to the shape of the ankle, can be inserted into the splint-mounting band (14).

A transverse aperture (22), through which an adhesion band, which serves as a splint fixing band (23), is looped, is provided on the lower end. It works together with just such a counter-band (43), which is attached on the medial splint (4) (FIG. 4). That splint (4) has a recess (41) in the ankle area, and is additionally provided there with a curvature (44) corresponding to the shape of the ankle. The counter-band (43) is again looped through a transverse aperture (42) in the lower edge area of the splint (4).

An eversion wedge (3) (see FIGS. 3a, 3b, and 6) can be applied in the bandage (1) onto the positioning band (17). This eversion wedge, which is preferably produced from a foamed material, such as, for example, a polyurethane foam, has two walls (31 and 32) forming approximately a right angle. While the vertical wall (31) has a thickness which remains approximately uniform over the entire surface, the horizontal plantar wall is tapered in a wedge-shaped manner. Both walls have on their outer or lower side, respectively, an adhesion band section (33, 34), which cooperates with the positioning band (17) which has already been described.

Finally, FIG. 5 additionally depicts an anti-plantar flexion band (5). This consists of a curving cut strip (51), which is preferably produced from plastic, synthetic leather or leather, and is provided with a padding layer. One elastic adhesion band is sewed on to each of the ends of band (5). While the medial adhesion band (52) is relatively short, the lateral adhesion band (53) is much longer.

The anti-plantar flexion band (5) has an anti-supination effect; that is to say, an effect directed against inversion. Thus, this band (5) may also be termed an anti-supination band.

During the first-time use of the orthotic device, the eversion wedge (3) is first applied, as FIG. 6 depicts. In this, the vertical wall (31) is, if necessary, shortened, and the wedgeshaped plantar wall (32) is so adapted, that it tapers down to nothing at the center of the sole of the foot. After that, the eversion wedge (3) is, along with its adhesion band sections (33 and 34), fitted into the bandage (1) and pressed down, so that the adhesion band section (33) on the positioning band (17) adheres to the lateral cloth piece (12), and the adhesion band section (34) on the positioning band (17) adheres to the plantar cloth piece (13).

In order to reduce the danger of embolism, an elastic support stocking is put on and the bandage (1) is then applied. Because of the great elasticity of the bandage, it is possible to make do with only three different sizes for adult patients. When the bands (16) are closed, the bandage (1) is tightly closed. After that, the medial and lateral splints, (2) and (4), respectively, are moved into the corresponding splint-mounting bands, (14) and (15), respectively, their correct position is secured, and these are then fixed, relative to one another, by means of the corresponding bands (23 and 43).

The relative position of the splint (2) is secured, relative to the bandage (1), by means of relatively long holding bands (24), which are in turn formed as elastic adhesion bands. The bands (24) hold an intermediate piece (26), which is attached by means of a rivet (25) to the lateral splint (2). The long holding bands (24) proceed helically around the bandage (1) and thereby cross the bands (14 and 15) which are formed as counterbands and serve as splint-mountings, to which bands they adhere. In this position, as is depicted in FIG. 7, the foot is supported by the splint (2 and 4), and held, by the eversion wedge 3, in a slight eversion position, and is thus protected against an inversion.

The strength of the bandage (1) also provides some security in regard to a plantar flexion. In the early healing stage, however, this is additionally secured by means of the anti-plantar flexion band (5). Its short adhesion band (52) is medially attached to the splint-mounting ban (14) and the curving strip (51) below the foot, placed from the medial side to the lateral side, and drawn, by means of the long lateral band (53), over the foot and onto the medial side again, by means of which the desired eversion is also further increased.

Patients whose ankle ligaments have already been injured once frequently tend repeatedly to sprains. In such cases, the patient will wear the present orthotic device, particularly during the playing of sports, even long after the healing of the injury. He can later, however, frequently dispense with the anti-plantar flexion band (5). The eversion wedge (3), however, must not be omitted.

I claim:

1. An improved orthotic device for the dynamic treatment of tears of the ligaments or of sprains of the lateral ankle, comprising in combination:

a bandage (1) of the leggings type with closing bands, said bandage formed of medial, lateral, and plantar textile cloth sections (11, 12, 13), said medial and lateral textile cloth sections (11, 12) being closable one to the other by said closing bands (16);

split mounting bands (14, 15) respectively mounted longitudinally of said bandage (1) on said medial and lateral textile cloth sections;

medial and lateral splints (2, 4) respectively inserted into said medial and lateral splint mounting bands (14, 15);

an eversion wedge (3) applied to said bandage (1), said wedge formed of two walls (31, 32) positioned at least approximately perpendicular to one another, the wall thereof in the plantar position (32) decreasing in a wedged-shaped manner from the wall thereof in the lateral position (31) to the middle of said plantar textile cloth section (13), whereby said eversion wedge (3) can be adjustably applied to said bandage (1) in a locally-variable manner in accordance with the shape of the foot to which the bandage (1) is to be fitted for support;

an anti-plantar flexion band (5) formed of a curving cut strip (51), said strip (51) terminating in one end in a medial adhesion band for adhering said strip (51) to said medial splint-mounting band (14), and terminating at the other end in an elongated lateral adhesion band (53), said strip (51) extending under said plantar textile cloth piece (13) and extending away from the lateral side of said bandage (1), said elongated lateral adhesion band (53) adapted to adhere said strip (51) to the medial side of said bandage (1) on said same splint-mounting band (14);

said medial splint (4) being held relative to said lateral splint (2) by splint-fixing bands (23, 43);

said eversion wedge (3) being provided, so as to apply said eversion wedge (3) to said bandage (1), with adhesion band sections (33, 34), and said bandage (1) has, on the internal surface thereof in the area of said plantar textile cloth piece (13) and said lateral textile cloth piece (12), a positioning band (17) to which said adhesion band sections (33, 34) adhere.

2. The improved orthotic device of claim 1, wherein said lateral splint (2) is fixed relative to said bandage (1) by means of two elongated elastic holding bands (24) interconnected to one another through an intermediate piece (26) which is attached to said lateral splint (2).

3. The improved orthotic device of claim 1, wherein said lateral splint (2) has a recession (21) for the ankle area of the foot which is to be supported.

4. The improved orthotic device of claim 1, wherein said medial splint (4) has a curvature (44) and a recess (41) for the ankle area of the foot which is to be supported.

* * * * *